United States Patent
Razzell et al.

(10) Patent No.: US 8,869,638 B2
(45) Date of Patent: Oct. 28, 2014

(54) INSPECTION OF PIPE INTERIOR

(75) Inventors: Anthony G. Razzell, Derby (GB);
Robert J. Mitchell, Derby (GB)

(73) Assignee: Rolls-Royce PLC, London (GB)

( * ) Notice: Subject to any disclaimer, the term of this patent is extended or adjusted under 35 U.S.C. 154(b) by 325 days.

(21) Appl. No.: 13/439,438

(22) Filed: Apr. 4, 2012

(65) Prior Publication Data

US 2012/0260735 A1    Oct. 18, 2012

(30) Foreign Application Priority Data

Apr. 15, 2011  (GB) .................................. 1106405.2

(51) Int. Cl.
| | |
|---|---|
| G01N 21/88 | (2006.01) |
| G01F 23/296 | (2006.01) |
| G01N 29/22 | (2006.01) |
| G01N 29/265 | (2006.01) |

(52) U.S. Cl.
CPC ............ *G01F 23/296* (2013.01); *G01N 29/222* (2013.01); *G01N 29/265* (2013.01); *G01N 2291/044* (2013.01)
USPC ........................................................ 73/865.8

(58) Field of Classification Search
None
See application file for complete search history.

(56) References Cited

U.S. PATENT DOCUMENTS

| | | | | |
|---|---|---|---|---|
| 4,084,436 | A | * | 4/1978 | Smitherman .................... 73/313 |
| 4,142,414 | A | * | 3/1979 | Cosentino ........................ 73/216 |
| 4,725,883 | A | | 2/1988 | Clark, Jr. et al. |
| 4,887,231 | A | | 12/1989 | Ratliff et al. |
| 5,092,176 | A | | 3/1992 | Buttram et al. |
| 5,408,874 | A | * | 4/1995 | Fleck et al. .................. 73/290 V |
| 5,604,531 | A | | 2/1997 | Iddan et al. |
| 6,020,918 | A | | 2/2000 | Murphy |
| 7,278,311 | B1 | * | 10/2007 | Demin ......................... 73/322.5 |
| 2009/0217753 | A1 | | 9/2009 | Burris |

FOREIGN PATENT DOCUMENTS

| | | | |
|---|---|---|---|
| GB | 1 524 042 | | 9/1978 |
| JP | 58006278 | * | 1/1983 |
| JP | A-10-332459 | | 12/1998 |
| JP | A-11-132764 | | 5/1999 |
| JP | 2005-37212 | * | 2/2005 |
| JP | A-2005-37212 | | 2/2005 |

(Continued)

OTHER PUBLICATIONS

Jul. 26, 2012 Search Report issued in European Patent Application No. EP 12 16 3115.

(Continued)

*Primary Examiner* — Robert R Raevis
(74) *Attorney, Agent, or Firm* — Oliff PLC

(57) ABSTRACT

A method for inspecting the interior of a non-horizontal pipe includes (a) filling the pipe with a first fluid, (b) feeding a second fluid into a lower part of the pipe when the second fluid is more dense than the first fluid or into an upper part of the pipe when the second fluid is less dense than the second fluid the pipe, a meniscus forming between the first and the second fluid and moving along the pipe, (c) introducing an inspection device having an average density between the densities of the first and second fluids such that the device locates at and moves with the meniscus, (d) obtaining inspection data from the inspection device as the device moves along the pipe, (e) determining positions of the meniscus as it moves along the pipe, and (f) relating the meniscus positions to positions at which the inspection data is obtained.

14 Claims, 2 Drawing Sheets

(56) References Cited

FOREIGN PATENT DOCUMENTS

Figure 1:
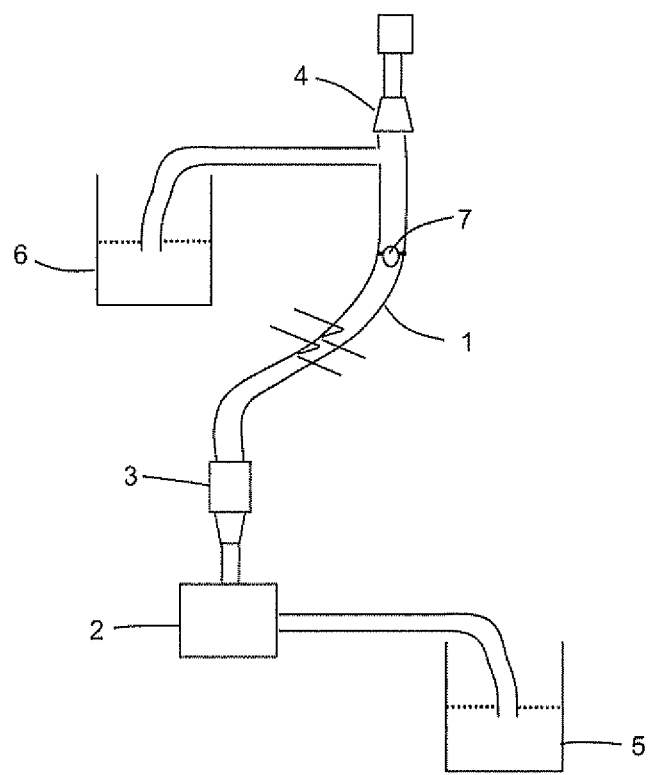

| | | |
|---|---|---|
| JP | A-2009-69136 | 4/2009 |
| JP | A-2009-198377 | 9/2009 |
| RU | 2 209 343 C2 | 7/2003 |
| SU | 1226056 A | 4/1986 |
| SU | 1768969 A1 | 10/1992 |

OTHER PUBLICATIONS

Jun. 22, 2012 Search Report issued in European Patent Application No. EP 12 16 3117.

Search Report issued in British Patent Application No. GB 1106404.5 dated May 27, 2011.

Search Report issued in British Patent Application No. GB 1106405.2 dated Jul. 15, 2011.

Kato, Shigeo et al., "Development of Inchworm Type Mobile Robot Movable in Pipes with T-Junction," Proc. of American Society for Precision Engineering, 2004 Annual Meeting, pp. 257-260.

U.S. Appl. No. 13/439,230, filed Apr. 4, 2012 in the name of Razzell et al.

U.S. Office Action dated May 8, 2014 from U.S. Appl. No. 13/439,230.

* cited by examiner

INSPECTION OF PIPE INTERIOR

The present invention relates to a method and system for inspecting the interior of a non-horizontal pipe.

Corrosion and the build up of deposits in the tubes and pipes of boilers and steam generators found in most power plants can affect the lifetime and performance of such components. It is thus desirable to be able to inspect the interior of such pipes, e.g. in order to implement an appropriate maintenance regime.

Further, as much of the exterior of the pipes may not be accessible, it is desirable that inspection can be achieved via access at, for example, only the ends of a pipe.

S. Kato, M. Kato, S. Ogawa and M. Ono, *Development of inchworm type mobile robot movable in pipes with T-junction*, Proc. of American Society for Precision Engineering, 2004 Annual Meeting, pp. 257-260 describes an inchworm style robot for inspecting pipes. The robot is powered by a cable connection to a source at the end of the pipe. However, the scale of the robot (33 mm diameter) is not small enough to work in many desired applications. Also, it would be desirable to avoid the need to power the robot by a cable connection.

Accordingly, in a first aspect, the present invention provides a method of inspecting the interior of a non-horizontal pipe, the method including the steps of:

(a) filling the pipe with a first fluid;

(b) feeding a second fluid into the pipe, the second fluid having a different density to the first fluid, the second fluid being fed into a lower part of the pipe when the second fluid is more dense than the first fluid or into an upper part of the pipe when the second fluid is less dense than the second fluid, a meniscus being formed between the first and the second fluid, and the meniscus moving along the pipe as the second fluid displaces the first fluid in the pipe;

(c) introducing an inspection device into the pipe, the device having an average density between the densities of the first and second fluids such that the device locates at and moves with the meniscus;

(d) obtaining inspection data from the inspection device as the device moves along the pipe;

(e) determining positions of the meniscus as it moves along the pipe; and (f) relating the meniscus positions to positions at which the inspection data is obtained Advantageously, the method allows internal inspection of the pipe without requiring external access to positions along the pipe. Further, there is no need for cabling to power the inspection device, and the inspection device can be sized to allow it to travel through relatively small diameter pipes.

The method may have any one or, to the extent that they are compatible, any combination of the following optional features.

The inspection device may obtain images of the interior of the pipe as the device moves along the pipe. For example, the device may be an endoscopic capsule of a known type used in medical applications to inspect the digestive system, as described for example in U.S. Pat. No. 5,604,531. Conventionally, such devices are swallowed and pass through the digestive system via peristalsis.

Conveniently, in step (e) the meniscus positions may be detected ultrasonically. For example, the meniscus positions can be detected by reflecting ultrasound off the meniscus, the ultrasound travelling to and from the meniscus along the fluid in the pipe.

Alternatively or additionally, in step (e), the flow rate of the second fluid into the pipe may be measured and the meniscus positions determined from the flow rate and a known cross-sectional area of the pipe.

Typically, the second fluid is immiscible with the first fluid and the meniscus can thus be formed at an interface between the first and the second fluid. For example, the first and second fluid can be benzene and water. The different velocities of sound in the different fluids will generally need to be taken into account when ultrasonically measuring meniscus position.

Alternatively, however, the method may further include, between steps (a) and (b), a step of feeding a volume of a third fluid into the pipe, the third fluid being immiscible with the first and second fluids such that respective menisci are formed at interfaces between the first and third fluids and between the second and third fluids, and the third fluid having a density intermediate the densities of the first and second fluids. In step (c), two inspection devices can then be introduced into the pipe, the first of the devices having an average density between the densities of the first and third fluids such that the first device locates at and moves with the meniscus at the interface between the first and third fluids, and the second device having an average density between the densities of the third and second fluids such that the second device locates at and moves with the meniscus at the interface between the third and second fluids. Further, in step (d), inspection data can be obtained from the first and second inspection devices as the devices move along the pipe, in step (e) the positions of both menisci can be determined as they move along the pipe, and in step (f) both menisci positions can be related to the positions at which the inspection data is obtained. The first, second and third fluids are typically different fluids, for example water, benzyl alcohol and decane. The relative menisci positions may be determined from a known volume of the third fluid introduced into the pipe and a known cross-sectional area of the pipe.

Although the fluids have different densities, preferably, they are sufficiently similar, to prevent buoyancy forces breaking the or each meniscus.

The pipe may be a boiler or steam generator pipe, or a fuel line.

Typically, the pipe has a 10 mm or less internal diameter. This helps to prevent buoyancy forces breaking the or each meniscus.

In a second aspect, the present invention provides a system for inspecting the interior of a non-horizontal pipe which is filled with a first fluid, the system including:

a pump for feeding a second fluid into the pipe, the second fluid having a different density to the first fluid, the second fluid being fed into a lower part of the pipe when the second fluid is more dense than the first fluid or into an upper part of the pipe when the second fluid is less dense than the second fluid, a meniscus being formed between the first and the second fluid, and the meniscus moving along the pipe as the second fluid displaces the first fluid in the pipe;

an inspection device for introduction into the pipe, the device having an average density between the densities of the first and second fluids such that the device locates at and moves with the meniscus; and a sub-system for determining positions of the meniscus as it moves along the pipe such that the meniscus positions can be related to the positions at which the inspection data is obtained.

Thus the system can be used to perform the method of the first aspect.

The system may have any one or, to the extent that they are compatible, any combination of the following optional features.

The inspection device may obtains images of the interior of the pipe as the device moves along the pipe. The device may have a diameter of 10 mm or less.

The sub-system may include an ultrasonic detector for ultrasonically detecting the meniscus positions of the as the meniscus moves along the pipe. For example, the ultrasonic detector can be configured to direct ultrasound along the fluid in the pipe, the ultrasound reflecting off the meniscus, and then returning along the fluid in the pipe to be detected by the detector.

Additionally, or alternatively, the sub-system can include a flow controller for measuring the flow rate of the second fluid into the pipe, the meniscus positions being determined from the flow rate and a known cross-sectional area of the pipe.

Figure 2:
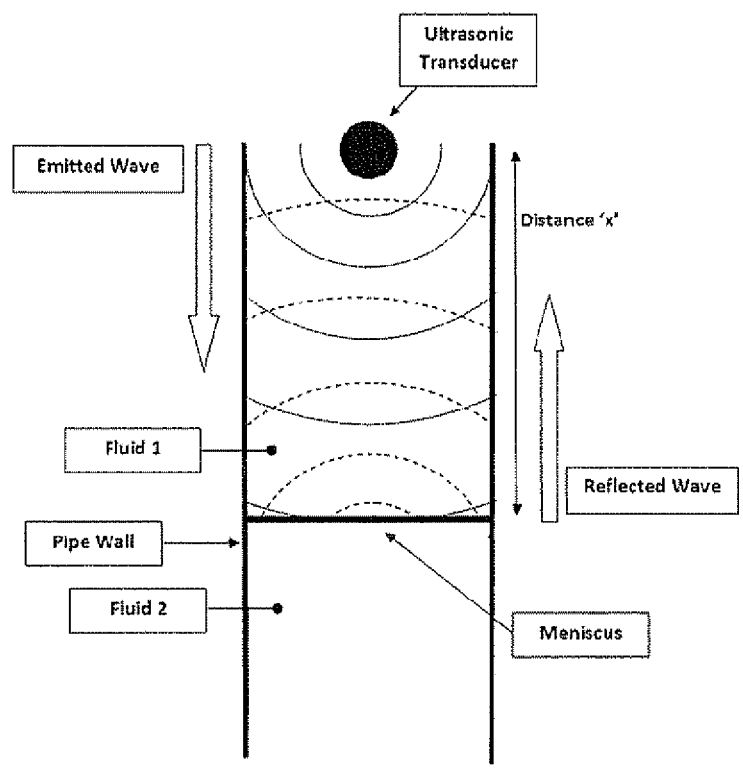

Embodiments of the invention will now be described by way of example with reference to the accompanying drawings in which:

FIG. 1 shows schematically a system for inspecting the interior of a non-horizontal pipe; and FIG. 2 shows a close up schematic view of the meniscus between the two fluids in the pipe of FIG. 1.

FIG. 1 shows schematically a system for inspecting the interior of a non-horizontal pipe 1. The pipe, for example a tube of a boiler or steam generator, is subject in use to internal deposit build up and corrosion. The system includes a pump 2 for pumping fluids into the pipe, a mass flow controller 3 for measuring the flow rate of the pumped fluids, and an ultrasonic liquid interface measuring device 4 for measuring ultrasonically the position of a meniscus within the pipe. Conveniently, the pump and the mass flow controller are located at a first (e.g. lower) end of the pipe and the ultrasonic measuring device at a second (upper) end. Fluid to be pumped into the pipe is held in a first reservoir 5 which fluidly communicates with the first end. A second reservoir 6 for receiving fluids which have passed through the pipe fluidly communicates with the second end.

Two immiscible fluids are prepared, for example water and benzene, which when deployed in the pipe form a meniscus at their interface. Desirably the fluids have close but dissimilar densities to prevent buoyancy forces breaking the meniscus. In the configuration of FIG. 1, the pipe is filled first with the lower density fluid. If the pipe were to be fed with the second fluid from the upper end, then it would be filled first with the higher density fluid. Typically, the pipe internal diameter is about 10 mm or less.

To use the system, first the pipe 1 is flushed through and filled with the first fluid (e.g. benzene). The pipe is then fed from the lower end with a small amount of the second fluid (e.g. water) such that a meniscus is formed at the lower end of the pipe between the fluids. An inspection device 7, such as an endoscopic capsule of known type, is then introduced into the pipe. The capsule has an average density between that of the first and second fluids. The average density can be adjusted, if necessary, by providing the device with ballast or a float. The device thus locates itself at the meniscus.

The second fluid is next fed into the pipe 1 at a known flow rate. This is accomplished by using the pump 2 to draw the second fluid from the first reservoir 5 into the first end of the pipe and using the mass flow controller 3 to measure the flow rate of the pumped second fluid. The first fluid displaced from the pipe is received in the second reservoir 6.

The meniscus moves up the pipe 1 as the second fluid is pumped in, and the inspection device 7 moves with it, taking images of the interior of the pipe. The flow rate of the second fluid can be controlled, as necessary, to speed up or slow down the passage of the device.

If the cross-sectional area of the pipe 1 is known, the meniscus position at any given time can be calculated from the flow rate of the second fluid (which gives the volume of fed second fluid) and the known cross-sectional area.

However, if the cross-sectional area of the pipe 1 is not known, or if a second determination of the meniscus position is desired, the position of the meniscus at any given time can be detected using the ultrasonic liquid interface measuring device 4. Suitable devices may be commercially available liquid level detectors of the type described in JP 10332459 A. These operate by transmitting an ultrasound down the fluid in the pipe and timing how long the reflection takes to return, as shown schematically in FIG. 2 (for clarity, the inspection device 7 is omitted from FIG. 2).

In this way the inspection data obtained by the device 7 can be related to the meniscus positions, and thereby to the pipe positions from which the data originated.

In a variant of the approach, a known volume of a third fluid is introduced into the pipe 1 (e.g. by the pump 2 and the mass flow controller 3) after the pipe is filled with the first fluid but before the feeding in of the second fluid. The third fluid, which has an intermediate density and is immiscible with the first and second fluids, thus forms a plug between the first and second fluids with a meniscus at each end of the plug. Two inspection devices can then be introduced into the pipe, the first device having an average density between the densities of the first and third fluids, and the second device having an average density between the densities of the third and second fluids. The devices thus locate at respective menisci. The positions of the menisci as the second fluid is fed in are determined as described above. For example, the ultrasonic measuring device 4 can obtain reflections from and measure the positions of both menisci. If the introduced volume of the third fluid and the cross-sectional area of the pipe are known, the relative distance between the two menisci can also be calculated.

Advantageously, the approach allows internal inspection of the pipe without access to the outside of the pipe. In particular, merely by feeding immiscible fluids through the pipe, controlled transportation of the inspection device can be achieved.

Although developed for use in the boiler pipes of nuclear power plants, the approach can be used to other situations where it is necessary to measure the internal cross-sectional area of a pipe and where it is possible to flush fluids through the pipe. For example, the approach may be used to measure cross-sectional areas of fuel lines.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

All references referred to above are hereby incorporated by reference.

The invention claimed is:

1. A method of inspecting the interior of a non-horizontal pipe, the method including the steps of:
   (a) filling the pipe with a first fluid;
   (b) feeding a second fluid into the pipe, the second fluid having a different density to the first fluid, the second fluid being fed into a lower part of the pipe when the second fluid is more dense than the first fluid or into an upper part of the pipe when the second fluid is less dense than the second fluid, a meniscus being formed between the first and the second fluid, and the meniscus moving along the pipe as the second fluid displaces the first fluid in the pipe;

(c) introducing an inspection device into the pipe, the device having an average density between the densities of the first and second fluids such that the device locates at and moves with the meniscus;

(d) obtaining inspection data relating to an interior of the pipe from the inspection device as the device moves along the pipe;

(e) determining positions of the meniscus as it moves along the pipe, wherein the meniscus positions are detected ultrasonically; and (f) relating the meniscus positions to positions at which the inspection data is obtained.

2. A method according to claim 1, wherein the inspection device obtains images of the interior of the pipe as the device moves along the pipe.

3. A method according to claim 1, wherein, in step (e), the meniscus positions are detected by reflecting ultrasound off the meniscus, the ultrasound travelling to and from the meniscus along the fluid in the pipe.

4. A method according to claim 1, wherein the second fluid is immiscible with the first fluid and the meniscus is formed at an interface between the first and the second fluids.

5. A method according to claim 1, further including, between steps (a) and (b), a step of feeding a volume of a third fluid into the pipe, the third fluid being immiscible with the first and second fluids such that respective menisci are formed at interfaces between the first and third fluids and between the second and third fluids, and the third fluid having a density intermediate the densities of the first and second fluids; and wherein:

in step (c), introducing two inspection devices into the pipe, the first of the devices having an average density between the densities of the first and third fluids such that the first device locates at and moves with the meniscus at the interface between the first and third fluids, and the second device having an average density between the densities of the third and second fluids such that the second device locates at and moves with the meniscus at the interface between the third and second fluids;

in step (d), obtaining inspection data relating to an interior of the pipe from the first and second inspection devices as the devices move along the pipe;

(e) determining the positions of the menisci as they move along the pipe, wherein the menisci positions are detected ultrasonically; and (f) relating the menisci positions to the positions at which the inspection data is obtained.

6. A method of inspecting the interior of a non-horizontal pipe, the method including the steps of:

(a) filling the pipe with a first fluid;

(b) feeding a second fluid into the pipe, the second fluid having a different density to the first fluid, the second fluid being fed into a lower part of the pipe when the second fluid is more dense than the first fluid or into an upper part of the pipe when the second fluid is less dense than the second fluid, a meniscus being formed between the first and the second fluid, and the meniscus moving along the pipe as the second fluid displaces the first fluid in the pipe;

(c) introducing an inspection device into the pipe, the device having an average density between the densities of the first and second fluids such that the device locates at and moves with the meniscus;

(d) obtaining inspection data relating to an interior of the pipe from the inspection device as the device moves along the pipe;

(e) determining positions of the meniscus as it moves along the pipe, wherein the flow rate of the second fluid into the pipe is measured and the meniscus positions are determined from the flow rate and a known cross-sectional area of the pipe; and (f) relating the meniscus positions to positions at which the inspection data is obtained.

7. A method according to claim 6, further including, between steps (a) and (b), a step of feeding a volume of a third fluid into the pipe, the third fluid being immiscible with the first and second fluids such that respective menisci are formed at interfaces between the first and third fluids and between the second and third fluids, and the third fluid having a density intermediate the densities of the first and second fluids; and wherein:

in step (c), introducing two inspection devices into the pipe, the first of the devices having an average density between the densities of the first and third fluids such that the first device locates at and moves with the meniscus at the interface between the first and third fluids, and the second device having an average density between the densities of the third and second fluids such that the second device locates at and moves with the meniscus at the interface between the third and second fluids;

in step (d), obtaining inspection data relating to an interior of the pipe from the first and second inspection devices as the devices move along the pipe;

(e) determining the positions of the menisci as they move along the pipe, wherein the relative menisci positions are determined from a known volume of the third fluid introduced into the pipe and a known cross-sectional area of the pipe; and (f) relating the menisci positions to the positions at which the inspection data is obtained.

8. A method according to claim 6, wherein the inspection device obtains images of the interior of the pipe as the device moves along the pipe.

9. A method according to claim 6, wherein the second fluid is immiscible with the first fluid and the meniscus is formed at an interface between the first and the second fluids.

10. A system for inspecting the interior of a non-horizontal pipe which is filled with a first fluid, the system including:

a pump for feeding a second fluid into the pipe, the second fluid having a different density to the first fluid, the second fluid being fed into a lower part of the pipe when the second fluid is more dense than the first fluid or into an upper part of the pipe when the second fluid is less dense than the second fluid, a meniscus being formed between the first and the second fluid, and the meniscus moving along the pipe as the second fluid displaces the first fluid in the pipe;

an inspection device for introduction into the pipe, the device having an average density between the densities of the first and second fluids such that the device locates at and moves with the meniscus, the inspection device being capable of obtaining inspection data relating to an interior of the pipe; and a sub-system for determining positions of the meniscus as it moves along the pipe such that the meniscus positions can be related to the positions at which the inspection data is obtained.

11. A system according to claim 10, wherein the inspection device obtains images of the interior of the pipe as the device moves along the pipe.

12. A system according to claim 10, wherein the sub-system includes an ultrasonic detector for ultrasonically detecting the meniscus positions of the as the meniscus moves along the pipe.

13. A system according to claim 12, wherein the ultrasonic detector is configured to direct ultrasound along the fluid in the pipe, the ultrasound reflecting off the meniscus, and then returning along the fluid in the pipe to be detected by the detector.

14. A system according to claim 10, wherein the sub-system includes a flow controller for measuring the flow rate of the second fluid into the pipe, the meniscus positions being determined from the flow rate and a known cross sectional area of the pipe.

\* \* \* \* \*